(12) United States Patent
Brown et al.

(10) Patent No.: US 10,851,037 B2
(45) Date of Patent: Dec. 1, 2020

(54) FAST PYROLYSIS OF BIOMASS IN AN AUTOTHERMALLY OPERATING REACTOR

(71) Applicant: Iowa State University Research Foundation, Inc., Ames, IA (US)

(72) Inventors: Robert C. Brown, Ames, IA (US); Joseph P. Polin, Ames, IA (US); Lysle E. Whitmer, Boone, IA (US)

(73) Assignee: IOWA STATE UNIVERSITY RESEARCH FOUNDATION, INC., Ames, IA (US)

( * ) Notice: Subject to any disclaimer, the term of this patent is extended or adjusted under 35 U.S.C. 154(b) by 281 days.

(21) Appl. No.: 15/798,056

(22) Filed: Oct. 30, 2017

(65) Prior Publication Data

US 2018/0118644 A1 May 3, 2018

Related U.S. Application Data

(60) Provisional application No. 62/414,953, filed on Oct. 31, 2016.

(51) Int. Cl.
| | |
|---|---|
| *C07C 1/20* | (2006.01) |
| *C07C 37/00* | (2006.01) |
| *C01B 32/05* | (2017.01) |
| *B01J 8/24* | (2006.01) |
| *C13K 1/02* | (2006.01) |
| *C13K 13/00* | (2006.01) |

(Continued)

(52) U.S. Cl.
CPC .............. *C07C 37/004* (2013.01); *B01J 8/24* (2013.01); *C01B 32/05* (2017.08); *C01B 32/40* (2017.08); *C01B 32/50* (2017.08); *C10B 49/02* (2013.01); *C10B 53/02* (2013.01); *C10C 5/00* (2013.01); *C10K 1/028* (2013.01); *C10K 1/04* (2013.01); *C11B 1/04* (2013.01); *C11B 1/10* (2013.01); *C11B 1/12* (2013.01); *C13K 1/02* (2013.01); *C13K 13/002* (2013.01); *Y02E 50/10* (2013.01)

(58) Field of Classification Search
None
See application file for complete search history.

(56) References Cited

U.S. PATENT DOCUMENTS 8,476,480 B1 * 7/2013 Brown ..................... C10K 1/04
585/240

FOREIGN PATENT DOCUMENTS

WO    WO-2016077695 A1 *  5/2016 ........... B01D 5/0087

OTHER PUBLICATIONS

Amutio et al., "Biomass Oxidative Flash Pyrolysis: Autothermal Operation, Yields and Product Properties," Energy and Fuels 26:1353-1362 (2012).

(Continued)

*Primary Examiner* — Philip Y Louie
(74) *Attorney, Agent, or Firm* — Troutman Pepper Hamilton Sanders LLP (Rochester)

(57) ABSTRACT

The present invention is directed to a pyrolysis method. The method involves providing a biomass and subjecting the biomass, in a reactor operating under conditions of parasitic heat loss of less than 1% of the biomass' chemical energy content, to partial oxidation where, during steady state operation of the reactor, oxygen is provided to the reactor in sufficient quantity to achieve an equivalence ratio of 0.06 to 0.15 to release sufficient energy to support endothermic pyrolysis reactions and produce condensable organic compounds as the major portion of the pyrolysis products.

23 Claims, 9 Drawing Sheets

(51) Int. Cl.
    C11B 1/12      (2006.01)
    C10B 49/02     (2006.01)
    C10B 53/02     (2006.01)
    C10C 5/00      (2006.01)
    C10K 1/02      (2006.01)
    C10K 1/04      (2006.01)
    C11B 1/10      (2006.01)
    C01B 32/40     (2017.01)
    C01B 32/50     (2017.01)
    C11B 1/04      (2006.01)

(56) References Cited

OTHER PUBLICATIONS

Amutio et al., "Kinetic Study of Lignocellulosic Biomass Oxidative Pyrolysis," Fuel 95:305-311 (2012).
Brown et al., "A Review of Cellulosic Biofuel Commercial-Scale Projects in the United States," Biofuels, Bioproducts and Biorefining 7(3):235-245 (2013).
Dalluge et al., "Continuous Production of Sugars from Pyrolysis of Acid-Infused Lignocellulosic Biomass," Green Chem. 16:4144-4155 (2014).
Daouk et al., "Thick Wood Particle Pyrolysis in an Oxidative Atmosphere," Chemical Engineering Science 126:608-15 (2015).
Daugaard and Brown, "Enthalpy for Pyrolysis for Several Types of Biomass," Energy and Fuels 17(4):934-939 (2003).
Gilbert et al., "Tar Reduction in Pyrolysis Vapours from Biomass Over a Hot Char Bed," Bioresource Technology 100:6045-51 (2009).
Hoekstra et al., "Fast Pyrolysis of Biomass in a Fluidized Bed Reactor: In Situ Filtering of the Vapors," Industrial & Engineering Chemistry Research 48:4744-56 (2009).
Kim et al., "Partial Oxidative Pyrolysis of Acid Infused Red Oak Using a Fluidized Bed Reactor to Produce Sugar-Rich Bio-Oil," Fuel 130:135-141 (2014).
Kim et al., "The Effect of Low-Concentration Oxygen in Sweep Gas During Pyrolysis of Red Oak Using a Fluidized Bed Reactor," Fuel 124:49-56 (2014).
Klein-Marcuschamer et al., "The Challenge of Enzyme Cost in the Production of Lignocellulosic Biofuels," Biotechnol. Bioeng. 109(4):1083-7 (2012).
Kuzhiyil et al., "Pyrolytic Sugars From Cellulosic Biomass," ChemSusChem 5(11):2228-36 (2012).
Li et al., "Autothermal Fast Pyrolysis of Birch Bark with Partial Oxidation in a Fluidized Bed Reactor," Fuel 121:27-38 (2014).
Mesa-Pérez et al., "Fast Oxidative Pyrolysis of Sugar Cane Straw in a Fluidized Bed Reactor," Applied Thermal Engineering 56:167-175 (2013).
Mullen et al., "Production of Deoxygenated Biomass Fast Pyrolysis Oils via Product Gas Recycling," Energy & Fuels 27:3867-3874 (2013).
Polin et al., "Investigation of Autothermal Operation of a Fluidized Bed Pyrolyzer," tcbiomass2015 Poster (Nov. 2-5, 2015).
Patwardhan et al., "Influence of Inorganic Salts on the Primary Pyrolysis Products of Cellulose," Bioresou.r Technol. 101(12):4646-55 (2010).
Patwardhan et al., Product Distribution from Fast Pyrolysis of Glucose-Based Carbohydrates, J. Anal. Appl. Pyrolysis 86(2):323-330 (2009).
Pollard et al., "Characterization of Bio-Oil Recovered as Stage Fractions with Unique Chemical and Physical Properties," J. Anal. Appl. Pyrolysis 93:129-138 (2012).
Rover et al., "Production of Clean Pyrolytic Sugars for Fermentation," ChemSusChem. 7(6):1662-8 (2014).
Rover et al., "The Effect of Pyrolysis Temperature on Recovery of Bio-Oil as Distinctive Stage Fractions," J. Anal. Appl. Pyrolysis 105:262-268 (2014).
Senneca et al., "Oxidative Pyrolysis of Solid Fuels," J. Anal. Appl. Pyrolysis 71:959-70 (2004).
Shen et al., "TG-MS Analysis for Thermal Decomposition of Cellulose Under Different Atmospheres," Carbohydrate Polymers 98:514-21 (2013).
Suárez et al., "Autothermal Fluidized Bed Pyrolysis of Cuban Pine Sawdust," Energy Sources, Part A: Recovery, Utilization, and Environmental Effects 28:695-704 (2006).
Sun et al., "Decomposition and Gasification of Pyrolysis Volatiles from Pine Wood through a Bed of Hot Char," Fuel 90:1041-8 (2011).
Wey et al., "Oxidative Pyrolysis of Mixed Solid Wastes by Sand Bed and Freeboard Reaction in a Fluidized Bed," Fuel 76:115-21 (1997).
Wongsiriamnuay et al., "Thermogravimetric Analysis of Giant Sensitive Plants Under Air Atmosphere," Biosource Tech. 101:9314-20 (2010).
Wright et al., "Distributed Processing of Biomass to Bio-Oil for Subsequent Production of Fischer-Tropsch Liquids," Biofuels, Bioprocessing, and Biorefineries 2:229-238 (2008).
Zhang et al., "Techno-Economic Analysis of Monosaccharide Production Via Fast Pyrolysis of Lignocellulose," Bioresour. Technol. 127:358-65 (2013).
Fundamentals of Engineering Thermodynamics, Fifth Edition by M. J. Moran & H. N. Shapiro (Wiley, 2004); pp. 138-141.
Fundamentals of Heat and Mass Transfer, Second Edition by F. P. Incropera & D. P. DeWitt (Wiley, 1985); pp. 3-6.
Kaczor et al., "Modelling Approaches to Waste Biomass Pyrolysis: A Review," Renewable Energy 159:427-443 (2020).
Van de Velden et al., "Fundamentals, Kinetics, and Endothermicity of the Biomass Pyrolysis Reaction," Renewable Energy 35:232-242 (2010).

* cited by examiner

US 10,851,037 B2

FAST PYROLYSIS OF BIOMASS IN AN AUTOTHERMALLY OPERATING REACTOR

This application claims the benefit of U.S. Provisional Patent Application Ser. No. 62/414,953, filed Oct. 31, 2016, which is hereby incorporated by reference in its entirety.

FIELD OF THE INVENTION

The present application relates to fast pyrolysis of biomass in an autothermally operating reactor.

BACKGROUND OF THE INVENTION

Pyrolysis as conventionally defined is the heating of biomass or other carbonaceous solids in the absence of oxygen to produce liquids (bio-oil), solids (char), and non-condensable gases (see, e.g., Brown et al., "Biorenewable Resources: Engineering New Products from Agriculture, Second Edition," Wiley Blackwell, Ames, Iowa, 215-26 (2003)). Slow pyrolysis, characterized by heating over several minutes or hours, favors dehydration reactions that yield char as the primary product. Fast pyrolysis strives to heat biomass to several hundred degrees Centigrade in a few seconds with the goal of maximizing bio-oil yield. Towards this end, biomass particles are finely ground, usually finer than a few millimeters diameter, and reactors are selected for their ability to sustain high heat fluxes at particle surfaces. Fluidized beds are particularly attractive for their ability to transfer heat between granular bed material and biomass particles although other schemes including screw augers and entrained flow reactors can also achieve rapid heating of biomass especially if used in conjunction with granular heat carriers. When using these kinds of reactors with finely ground particles, transferring heat to the surface of the biomass is rarely a constraint in pyrolysis.

More challenging is transferring heat into the pyrolyzer itself. Although the enthalpy for pyrolysis is relatively small (comparable to the enthalpy of evaporation for methanol) (Daugaard et al., "Enthalpy for Pyrolysis for Several Types of Biomass," *Energy and Fuels* 17(4):934-9 (2003)), heat fluxes in commercial-scale reactors are constrained by the need to heat a pyrolyzer to around 500° C., which limits heat carriers to inert gases like nitrogen or carbon dioxide and granular media like sand or steel shot. Gases are easy to handle but have limited volumetric heat capacities and heat transfer coefficients. Direct contact heat transfer is usually not practical because of the large volume of gas required. Instead, tubular heat exchangers are employed, although these are susceptible to erosion in fluidized pyrolyzers. Granular media have somewhat better thermal properties and are suitable for direct contact heat transfer but are more difficult to convey and the granular media becomes intermingled with solid products of pyrolysis. Both types of heat carrier require ancillary equipment to circulate and heat them. While they can provide significant heat transfer enhancement, heat exchangers and granular heat carriers also reduce the free volume of the reactor, ultimately decreasing the amount of biomass that otherwise could be processed.

Supplying the enthalpy of pyrolysis through heat transfer becomes increasingly difficult as the reactor becomes larger. As illustrated in FIG. 1, heat transfer only increases as the square of reactor diameter regardless of how heat is conveyed into the reactor (assuming a fixed diameter-to-length ratio). As the reactor becomes larger, energy demand for pyrolysis, which is a volumetric process, outstrips energy supply from heat transfer. With heat transfer rate limiting, the capacity of the reactor only scales as the square of diameter. Since both cost and capacity of the reactor roughly increase as the square of diameter, no economies of scale can be captured by building larger pyrolyzers (that is, cost increases linearly with capacity).

An autothermal reactor balances the energy demand of endothermic reactions with the energy released from exothermic reactions. Heat carriers, heat exchangers, and the associated ancillary equipment can be eliminated. Since chemical reaction rather than heat transfer controls the overall process, capacity scales as the cube of reactor diameter. If successfully applied to pyrolysis, it would represent a dramatic step in process intensification: an autothermal pyrolyzer would have several fold higher capacity to process biomass than conventional pyrolyzers of similar dimensions.

Autothermal operation is widely practiced in gasification of solid fuels and steam reforming of gaseous fuels. A small amount of oxygen is burned in these reactors to provide the energy required to drive the process toward equilibrium, producing a mixture of light, flammable gases known as syngas (primary carbon monoxide and hydrogen). The benefit of adding oxygen to a pyrolyzer is less obvious. If oxygen attacked anhydrosugars, phenolic monomers, and other heavy molecular species, pyrolysis products would undesirably include more light gases and less bio-oil.

Only a few researchers have explored the addition of oxygen to pyrolyzers. Kim et al., "The Effect of Low-Concentration Oxygen in Sweep Gas During Pyrolysis of Red Oak Using a Fluidized Bed Reactor," *Fuel* 124:49-56 (2014) and Kim et al., "Partial Oxidative Pyrolysis of Acid Infused Red Oak Using a Fluidized Bed Reactor to Produce Sugar-Rich Bio-Oil," *Fuel* 13:135-141 (2014) found that small amounts of oxygen actually increased yields of levoglucosan during continuous pyrolysis in a fluidized pyrolyzer, which was attributed to partial oxidation of the lignin sheath, allowing levoglucosan to more readily escape before it decomposed. Other researchers have admitted mixtures of nitrogen and oxygen into fluidized bed reactors to explore the feasibility of autothermal pyrolysis (Mesa-Pérez et al., "Fast Oxidative Pyrolysis of Sugar Cane Straw in a Fluidized Bed Reactor," *Appl. Therm. Eng.* 56:167-175 (2013) and Li et al., "Autothermal Fast Pyrolysis of Birch Bark with Partial Oxidation in a Fluidized Bed Reactor," *Fuel* 121:27-38 (2014)). Although autothermal operation was achieved, in both cases liquid yields suffered by as much as 30%. In one case, this poor performance was due to large parasitic heat losses in the small laboratory reactor used for the experiments (Mesa-Pérez et al., "Fast Oxidative Pyrolysis of Sugar Cane Straw in a Fluidized Bed Reactor," *Appl. Therm. Eng.* 56:167-175 (2013)). In the other case, it appears that the design of the freeboard of the fluidized bed inadvertently encouraged vapor degradation before it exited the reactor (Li et al., "Autothermal Fast Pyrolysis of Birch Bark with Partial Oxidation in a Fluidized Bed Reactor," *Fuel* 121:27-38 (2014)).

The present invention is directed to overcoming the above-noted deficiencies in the art.

SUMMARY OF THE INVENTION

The present invention is directed to a pyrolysis method. The method involves providing a biomass and subjecting the biomass, in a reactor operating under conditions of parasitic heat loss of less than 1% of the biomass' chemical energy content, to partial oxidation where, during steady state operation of the reactor, oxygen is provided to the reactor in sufficient quantity to achieve an equivalence ratio of 0.06 to 0.15 to release sufficient energy to support endothermic pyrolysis reactions and produce condensable organic compounds as the major portion of the pyrolysis products.

The Examples of the present application describe the partial oxidation of biomass or pyrolysis products to provide the enthalpy of pyrolysis in a fluidized bed reactor, a process that can be described as autothermal pyrolysis. The amount of oxygen depends upon the biomass being pyrolyzed and parasitic heat losses for the reactor, but under conditions that simulate adiabatic operation, equivalence ratios, defined as the ratio of oxygen used in the reactor to the oxygen required for stoichiometric combustion of the biomass, will be in the range of 0.06 to 0.15, compared to 0.20 or higher for autothermal gasifiers and greater than 1.0 to achieve complete combustion to carbon dioxide and water. For these low equivalence ratios, there is little or no loss in bio-oil yield or quality. Because autothermal pyrolysis is not limited by heat transfer as in a conventional pyrolyzer, much larger amounts of biomass can be processed in a reactor of given size. For example, a fluidized bed pyrolyzer operated in autothermal mode can process 4-5 times as much biomass as a similarly sized fluidized bed operated in a conventional mode (where no oxygen is added). In fact, throughput can be so large that the pyrolyzer can be "air blown" (100% air as the fluidization/ventilation gas). At these very high throughputs, the yield of bio-oil actually increases, especially for anhydrosugars and phenolic oil. Applicants' analysis indicates that oxidation of non-condensable gas species (CO, $CH_4$, $C_2H_6$, and $C_2H_4$) released during pyrolysis provided about half the energy for pyrolysis while the remainder of the energy is thought to come from the partial oxidation of lignin. In sum, the present invention results in the ability to achieve a pyrolysis reaction without heat transfer being the rate limiting step.

DETAILED DESCRIPTION OF THE INVENTION

Figure 1:
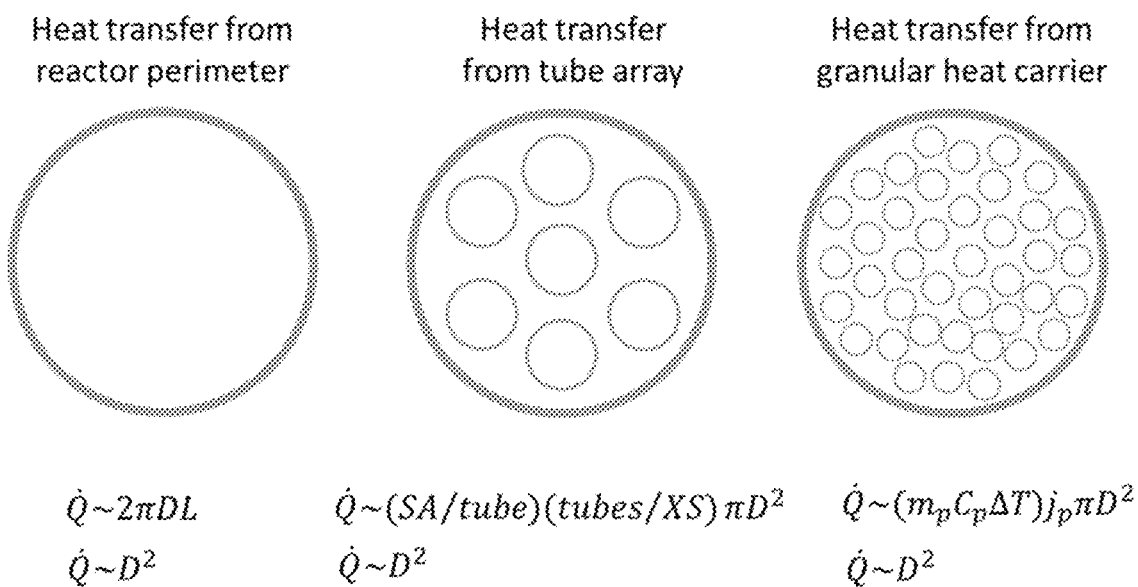
FIG. 1 illustrates the external heat transfer from cylindrical pyrolyzer of fixed diameter. The external heat transfer into a cylindrical pyrolyzer of fixed diameter to length ratio is proportional to the square of reactor diameter D regardless of how this heat is delivered (L: reactor length; SA/tube: surface area of a heat transfer tube in the reactor; tubes/XS: number of tubes per cross-sectional area of the reactor; $m_p C_p \Delta T$: sensible energy per particle of granular heat carrier; $j_p$: particle flux of granular heat carrier entering the reactor).

The present invention is directed to a pyrolysis method. The method involves providing a biomass and subjecting the biomass, in a reactor operating under conditions of parasitic heat loss of less than 1% of the biomass' chemical energy content, to partial oxidation where, during steady state operation of the reactor, oxygen is provided to the reactor in sufficient quantity to achieve an equivalence ratio of 0.06 to 0.15 to release sufficient energy to support endothermic pyrolysis reactions and produce condensable organic compounds as the major portion of the pyrolysis products.

In one embodiment, the reactor operates under conditions of parasitic heat loss less than 0.9%, less than 0.8%, less than 0.7%, less than 0.6%, less than 0.5%, less than 0.4%, less than 0.3%, less than 0.2%, or less than 0.1% of the chemical energy of the biomass.

As used herein, the term "adiabatic" or "adiabatically" refers to a process that occurs without transfer of heat or matter between a thermodynamic system and its surroundings.

As used herein, the term "autothermally" refers to a process where energy release of the exothermic reaction(s) within a reactor balances the energy demand of the endothermic reaction(s) within the reactor. During steady state operation, the reactor may operate autothermally under conditions that minimize parasitic heat loss and approach adiabatic operation.

As used herein, the term "process intensification" refers to the increase in biomass throughput in a reactor of given size. In one embodiment, the subjecting step is carried out within the reactor at a level of biomass throughput having a value proportional to more than the reactor diameter squared. The subjecting step can be carried out within the reactor at a level of biomass throughput up to, and optionally including, the reactor's diameter cubed.

Parasitic heat losses may also be minimized by increasing reactor diameter, thermally insulating the reactor, and combinations thereof.

As used herein, the term "pyrolysis" refers to the thermal decomposition of organic materials in an oxygen-poor atmosphere (i.e., significantly less oxygen than required for complete combustion). Slow pyrolysis produces large amounts of char (which can be used as a solid fuel), whereas fast pyrolysis produces condensable organic compounds (which may be condensed to bio-oil), gas (e.g., CO, $H_2$, $CO_2$, and $CH_4$), and char.

As used herein, the term "bio-oil" refers to a mixture of liquid organic materials obtained by conversion of biomass.

Bio-oil may comprise water, light volatiles, and non-volatiles, and significant quantities of oxygen-containing compounds. In one example, the decomposition of cellulose, hemicellulose, and/or lignin may result in various compounds including, but not limited to, hydroxy-aldehydes, hydroxyketones, sugars, carboxylic acids, and phenolics. The abundance of these chemical species in bio-oil makes it similar to crude petroleum oil, and thus an attractive resource for obtaining chemicals and fuels.

As used herein, the term "partial oxidation" relates to a process in which the biomass is supplied with less than the stoichiometric amount of oxygen needed for complete combustion.

As used herein, the term "equivalence ratio" refers to the ratio of oxygen input-to-oxygen required for stoichiometric combustion of the biomass.

During fast pyrolysis, dry biomass particles are rapidly heated to high temperatures in a reactor to produce various reaction products, including char, non-condensable gases (NCGs), aerosols, and condensable organic compounds (which may be condensed to produce a bio-oil product).

NGCs include, but are not limited to, hydrogen, carbon monoxide, carbon dioxide, and light hydrocarbons created during pyrolysis.

Aerosols are micron and submicron liquid droplets of organic compounds that either have too high a boiling point to evaporate in the pyrolyzer or have condensed from vapor after leaving the reactor because the gas stream has cooled. Aerosols may comprise carbohydrates, highly substituted phenolic compounds, and lignin oligomers.

Condensable organic compounds include, but are not limited to, water and organic compounds that are volatile at pyrolysis temperatures (e.g., carboxylic acids, alcohols, esters and phenolic compounds).

In one embodiment, the condensable organic compounds have a residence time in the reactor of 2-5 seconds.

Partial oxidation may be carried out using any suitable oxygen source, including, but not limited to, pure oxygen, oxygen-enriched air, and air. In one embodiment, the partial oxidation is carried out with air or air/nitrogen mixtures. In another embodiment, the partial oxidation is carried out with air.

The subjecting step may be carried out in a well-mixed reactor. An exemplary well-mixed reactor is a fluidized bed reactor.

Compared to other types of reactors (e.g., fixed bed reactors), fluidized bed reactors have a number of advantages, including the large gas-solid interface area and the nearly isothermal temperature distribution even for highly exothermal reactions. Moreover, fluidized beds have excellent particle mixing and gas-solid contacting. Gas-solid mixing not only enhances mass transfer, but also the heat transfer to internal surfaces (e.g., reactor walls, heat exchanger tubes, etc.) and between particles and the gas.

In one embodiment, the reactor is a fluidized reactor selected from the group consisting of a bubbling fluidized bed reactor, a circulating fluidized bed reactor, and a fast fluidized bed reactor.

The well-mixed reactor may alternatively include a mechanical agitator to mix material within the reactor. In one embodiment, material within the reactor can be stirred with an agitator selected from the group consisting of a fighting, an auger, a propeller, a paddle, and a ribbon.

In one embodiment, the production of condensible organic compounds is achieved with little or no loss in bio-oil yield or quantity compared to when oxygen is not provided to the reactor.

The major portion of the pyrolysis may comprise at least about 50%, 55%, 60%, 65%, 70%, or 75% of the total pyrolysis products. In one embodiment, the major portion of the pyrolysis products comprises at least about 50% of the total pyrolysis products. The major portion of the pyrolysis products comprises bio-oil. In one embodiment, the major portion of the pyrolysis comprises at least about 50% of the total pyrolysis products.

In another embodiment, the major portion of the pyrolysis comprised bio-oil.

As used herein, the term "biomass" refers to any organic source of energy or chemicals that is renewable. In one embodiment, the biomass is selected from the group consisting of forest and mill residues, agricultural crops and wastes, wood and wood wastes, grasses, manure, livestock operation residues, fast-growing trees and plants, and municipal and industrial wastes. In one example, biomass includes cellulose, hemicellulose, and/or lignin.

The subjecting step may be carried out at a temperature of 400 to 600° C.

The method may further involve recovering the condensable organic compounds after the subjecting step. In one embodiment, the recovered condensable organic compounds contain 5 to 15 wt % pyrolytic sugars. Exemplary pyrolytic sugars include, but are not limited to, levoglucosan and cellobiosan.

In another embodiment, the recovered condensable organic compounds contain 45 to 60 wt % phenolics.

The method may further involve recovering biochar produced in the reactor after the subjecting step.

In one embodiment, the reactor is provided with a heater to enable the reactor to reach steady state operation and enable the reactor to operate adiabatically during such steady state operation.

As used herein, the term "steady state" refers to operation of the reactor once it has been heated to normal operating temperatures and processes biomass into bio-oil products at full operational levels.

The recovery of bio-oil fractions can be carried out in accordance with the teachings of U.S. Pat. No. 8,476,480 to Brown et al., which is hereby incorporated by reference in its entirety.

In another embodiment, the subjecting step produces condensable organic compounds and the method further involves cooling the condensable organic compounds in a first stage comprising a condenser having passages for the condensable organic compounds separated by a heat conducting wall from passages for a coolant, where the coolant in the condenser of the first stage is maintained at a substantially constant temperature, set at a temperature in the range of 75 to 130° C., to condense a first liquid fraction of liquefied bio-oil constituents in the condenser of the first stage and collecting the first liquid fraction of liquefied bio-oil constituents from the condenser of the first stage.

In accordance with this embodiment, the method may further involve recovering a first bio-oil vapor fraction from the condenser of the first stage and removing aerosols from the first bio-oil vapor fraction in a second stage as a second liquid fraction of liquefied bio-oil constituents. The removing may be carried out without further cooling the first bio-oil vapor fraction. In one embodiment, the removing is carried out with an electrostatic precipitator.

The method may further involve recovering a second bio-oil vapor fraction after the removing aerosols step; cooling the second bio-oil vapor fraction in a third stage comprising a condenser having passages for the second bio-oil vapor fraction separated by a heat conducting wall from passages for a coolant, where the coolant in the condenser of the third stage is maintained at a substantially constant temperature, set at a temperature above the dew point of water, to condense a third liquid fraction of liquefied bio-oil constituents in the condenser of the third stage; and collecting the third liquid fraction of liquefied bio-oil constituents from the condenser of the third stage.

In accordance with this embodiment, the method further involves recovering a third bio-oil vapor fraction from the third stage and removing aerosols from the third bio-oil vapor fraction in a fourth stage as a fourth liquid fraction of liquefied bio-oil constituents. Removing aerosols from the third bio-oil vapor fraction may be carried out without further cooling the third bio-oil vapor fraction. In one embodiment, removing aerosols from the third bio-oil vapor fraction is carried out with an electrostatic precipitator.

The method may further involve recovering a fourth bio-oil vapor fraction after said removing aerosols from the third bio-oil vapor fraction; cooling the fourth bio-oil vapor fraction in a condenser of a fifth stage having passages for the fourth bio-oil vapor separated by a heat conducting wall from passages for a coolant, where the coolant in the condenser of the fifth stage is maintained at a substantially constant temperature, with a temperature set sufficiently low to condense substantially all water vapor from the fourth bio-oil vapor as a fifth liquid fraction of liquefied bio-oil constituents in the condenser of the fifth stage; and collecting the fifth liquid fraction of liquefied bio-oil constituents from the condenser of the fifth stage.

In one embodiment, the subjecting produces condensable organic compounds and the method further involves cooling the condensable organic compounds in a liquid scrubbing system to condense a first liquid fraction of liquefied bio-oil constituents and collecting the first liquid fraction of liquefied bio-oil constituents from the liquid scrubbing system. The liquid scrubbing system may be controlled as a function of the temperature of the condensable organic compounds entering the liquid scrubbing system. This method may further involve recovering a first bio-oil vapor fraction from the liquid scrubbing system and removing aerosols from the first bio-oil vapor fraction in a second stage as a second liquid fraction of liquefied bio-oil constituents.

In one embodiment, the removing is carried out without further cooling the first bio-oil vapor fraction. In another embodiment, the removing is carried out with an electrostatic precipitator.

Figure 2:
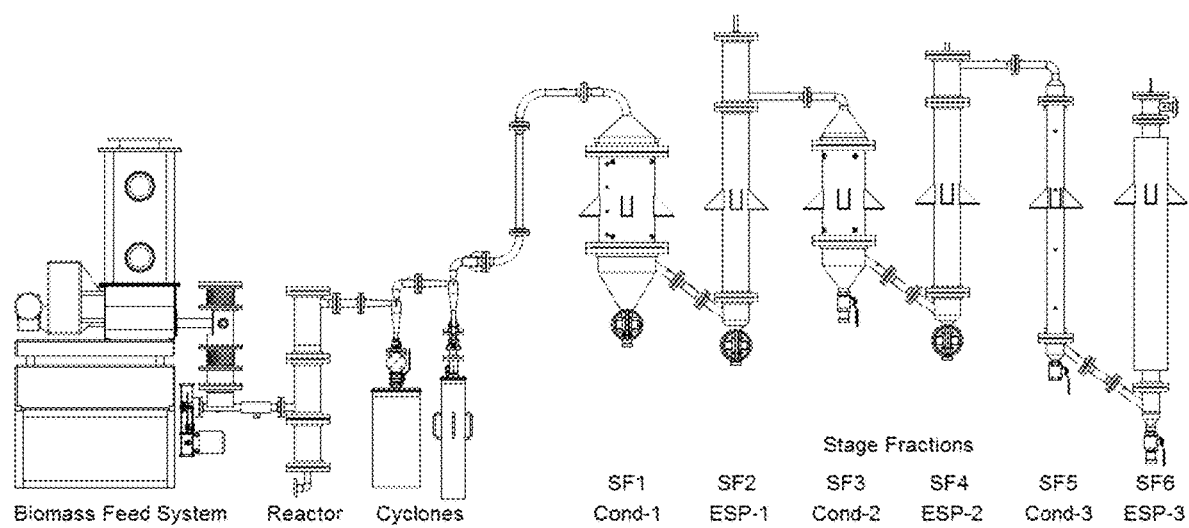
FIG. 2 is a schematic illustration of the Pyrolysis Process Development Unit (PPDU). The PPDU comprises a biomass feed system, a bubbling fluidized bed reactor, two cyclones for char collection, and a stage fractionation system, which collects fractionated bio-oil samples based on boiling point ranges. Stage fractions 1 and 2 (SF1 and SF2) are designed to collect heavy molecular weight bio-oil species commonly referred to as bio-oil heavy ends. Similarly, stage fractions 3 and 4 (SF3 and SF4) collect an intermediate mix of medium weight bio-oil compounds while stage fractions 5 and 6 (SF5 and SF6) collect the majority of light, aqueous and acidic bio-oil species; these stage fraction pairs are commonly referred to as middle ends and light ends, respectively.

In one example, the method of the present application can be carried out using the apparatus of FIG. 2, which comprises a biomass feed system, a bubbling fluidized bed reactor, two cyclones for char collection, and a stage fractionation system, which collects fractionated bio-oil samples based on boiling point ranges. During operation, the biomass feed system provides feed to the reactor, which is converted into a product stream comprising non-condensable gases, condensable organic compounds, and aerosols. Condensable organic compounds are cooled in sequential condensers and collected as separate stage fractions. Stage fractions 1 and 2 (SF1 and SF2) are designed to collect heavy molecular weight bio-oil species commonly referred to as bio-oil heavy ends. Similarly, stage fractions 3 and 4 (SF3 and SF4) collect an intermediate mix of medium weight bio-oil compounds while stage fractions 5 and 6 (SF5 and SF6) collect the majority of light, aqueous and acidic bio-oil species; these stage fraction pairs are commonly referred to as middle ends and light ends, respectively.

EXAMPLES

Example 1

Materials and Methods

The Examples of the present application utilized the Pyrolysis Process Development Unit (PPDU) located at the BioCentury Research Farm (BCRF) in Boone, Iowa, as previously described in Pollard et al., "Characterization of Bio-Oil Recovered as Stage Fractions with Unique Chemical and Physical Properties," *J. Anal. Appl. Pyrol.* 93:129-138 (2012), which is hereby incorporated by reference in its entirety (FIG. 2). The remaining gaseous product stream was analyzed by Gas Chromatography before flaring off. Prior to experiments, red oak biomass was prepared at the BCRF by drying *Quercus Rubra* wood chips to 10% or less moisture content and reducing its particle size using a hammer mill with a ⅛-inch screen insert. Mass balance data was collected using the feed system scale and recording container weights for pyrolysis products before and after steady state.

Figure 3:
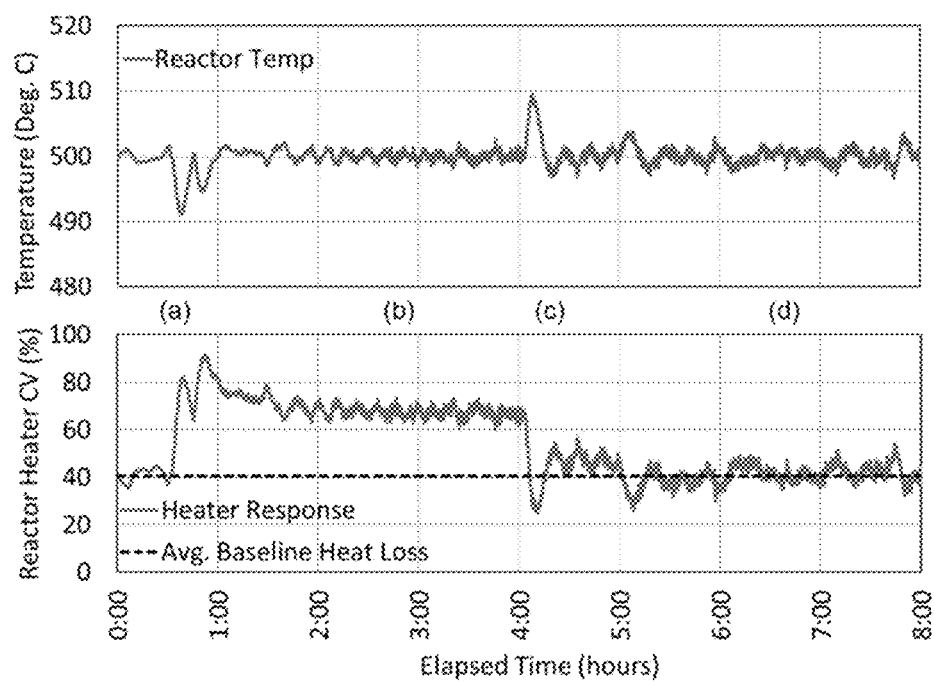
FIG. 3 illustrates the stages of an experiment, including the (a) starting biomass feed, (b) $N_2$ pyrolysis steady state, (c) stepping in air fluidizing gas, autothermal transition, and (d) autothermal pyrolysis steady state.

Before biomass was fed to the reactor, baseline heat losses were established by measuring the energy usage of clamshell electric heaters to maintain an internal process temperature of 500° C. The plenum and freeboard heaters' set points were then held constant at these levels to offset observed heat losses and simulate adiabatic conditions; this also helped isolate system responses to be counteracted solely by the bed heaters. Once the biomass feed started (FIG. 3, section (a)), the reactor temperature rapidly decreased to 490° C. but the bed heaters responded by increasing the heater's control variable (CV) percentage to regain temperature control at 500° C. This increase in heater response during $N_2$ pyrolysis steady state allowed the measurement for the enthalpy of pyrolysis of red oak, $H_P$=1141.8±58.5 J $g^{-1}$ (FIG. 3, section (b)). After steady state bio-oil and biochar samples ($N_2$) were collected, air was introduced as a portion of fluidizing gas and adjusted to provide enough internal heating and reduce the heater CV back to the baseline value. This occurred while the reactor continued operation at 500° C. with constant biomass feed at 5 kg $hr^{-1}$ (FIG. 3, section (c)). Another set of steady state bio-oil and biochar samples (AT) were later collected under these autothermal conditions (FIG. 3, section (d)). The AT-PI runs had a slightly different start-up procedure in which the biomass feed and fluidizing air were both increased, while maintaining the baseline heater CV, until the fluidizing gas was only air. At this point, the biomass feed reached 24 kg $hr^{-1}$ and steady state bio-oil and biochar samples were collected.

Example 2

Figure 4:
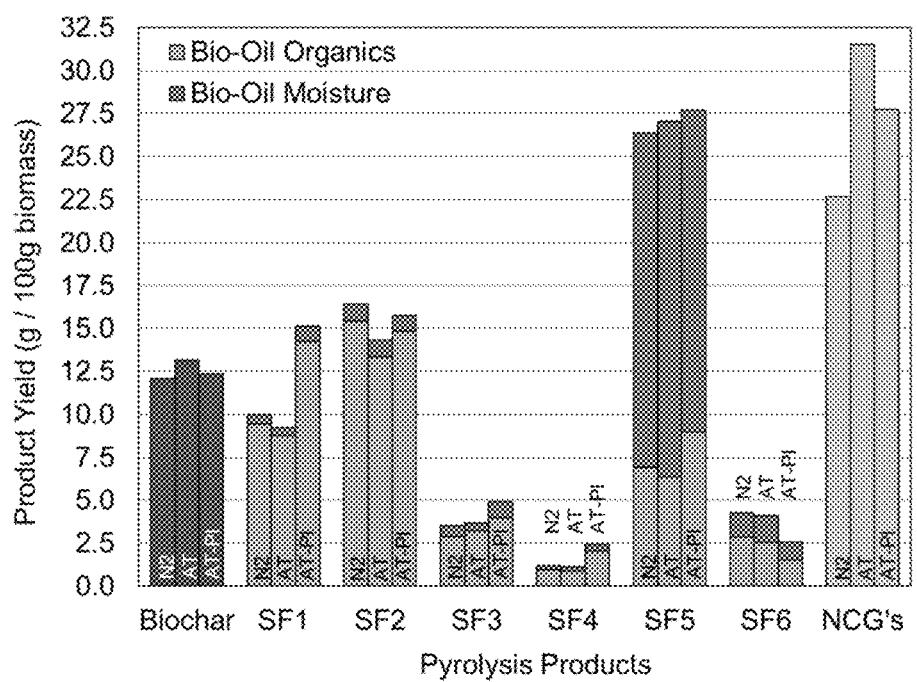
FIG. 4 shows a comparison of pyrolysis product distributions from nitrogen pyrolysis ($N_2$), autothermal pyrolysis (AT), and autothermal process intensification (AT-PI).

Collection and Analysis of Red Oak Steady State Products Under $N_2$, AT, and AT-PI Pyrolysis Conditions The pyrolysis products were collected at steady state for different pyrolysis conditions; $N_2$ pyrolysis, AT pyrolysis, and AT-PI; and a comparison of the mass balances can be seen in FIG. 4. The $N_2$ pyrolysis conditions served as a baseline to compare product yields of biochar, bio-oil collected from individual stage fractions, and NCGs. Biochar yields were found to be marginally affected by AT and AT-PI conditions whereas the bio-oil yields from all stage fractions and NCGs varied significantly. The bio-oil samples' moisture contents were measured by Karl Fischer Analyses and the bio-oil organics content was determined by difference. Compared to baseline $N_2$ pyrolysis conditions, the AT yields of bio-oil heavy ends (SF1 and SF2) seem to decrease slightly while a significant increase in NCG yields can be seen. This suggests that heavy molecular weight bio-oil compounds are combusted to produce additional NCGs during AT operation. This phenomenon appears to be non-existent during AT-PI and leads to much higher yields of bio-oil recovered in SF1 with an intermediate yield of NCGs.

Ultimate analyses of the red oak biomass, biochar, and bio-oil samples were performed using an Elemental Analyzer (vario MICRO cube) to measure the amounts of carbon, hydrogen, nitrogen, sulfur, and oxygen by difference. The amount of carbon remaining in the NCGs was determined by its composition of carbon-containing species; $CO_2$, $CO$, $CH_4$, $C_2H_4$, and $C_2H_6$; from gas chromatography.

Example 3

Figure 5:
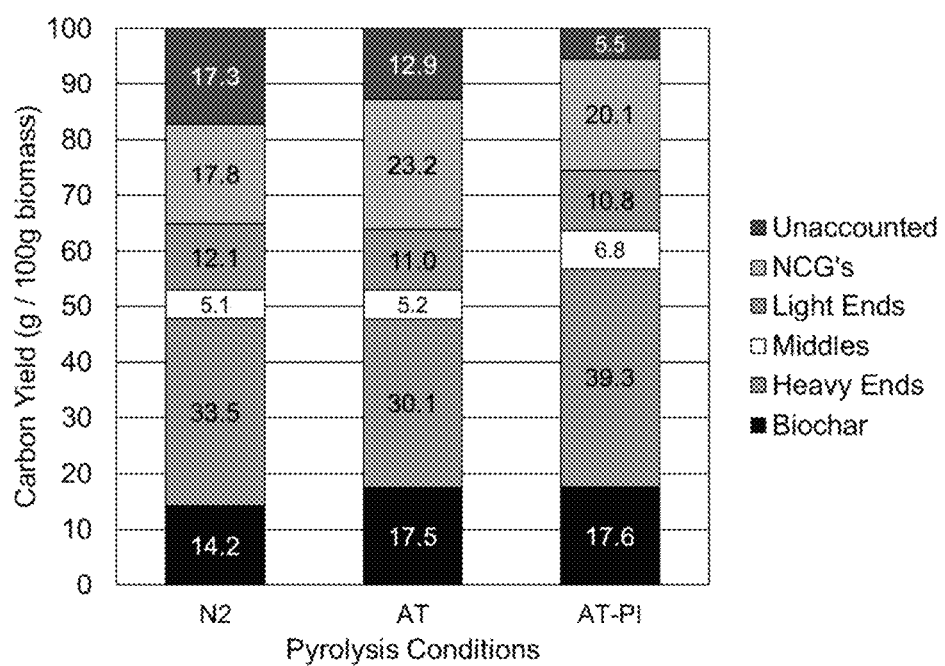
FIG. 5 shows a comparison of carbon balances from nitrogen pyrolysis (N2), autothermal pyrolysis (AT), and autothermal process intensification (AT-PI).

Carbon Yields from Red Oak Biomass Pyrolysis Under $N_2$ Pyrolysis, AT Pyrolysis, and AT-PI Conditions Carbon yields of biochar, bio-oil heavy ends, middle ends, light ends, and NCGs were calculated to compare the overall carbon balances of different pyrolysis conditions seen in FIG. 5. The unaccounted fraction was determined by the difference between the original carbon in red oak biomass and the sum of carbon collected in all pyrolysis products. The carbon yield of bio-oil heavy ends was highest during AT-PI conditions compared to $N_2$ and AT conditions and can be attributed to SF1's high mass yield from FIG. 5. It's worth noting that the unaccounted fraction decreases from $N_2$ to AT and exhibits its lowest amount during AT-PI. This unaccounted fraction represents potential carbonaceous deposits that require extensive cleaning between experimental runs, and its' reduction appears to enhance bio-oil collection from SF1.

Analysis of pyrolysis products collected in various stage fractions under AT-PI conditions is shown in Table 1.

TABLE 1

All values are presented as average weight %
on red oak biomass basis (g/100 g biomass)

| AT-PI Product Description | SF1 | SF2 | SF3 | SF4 | SF5 | SF6 | Totals |
|---|---|---|---|---|---|---|---|
| Bio-oil | 15.1 | 15.8 | 4.9 | 2.4 | 27.7 | 2.6 | 68.48 |
| Moisture | 0.87 | 0.90 | 0.95 | 0.33 | 18.74 | 1.09 | 22.89 |
| Organics | 14.25 | 14.86 | 3.97 | 2.06 | 8.97 | 1.48 | 45.59 |
| Pyrolytic Sugars | 3.48 | 5.24 | — | — | — | — | 8.72 |
| Phenolic Oil | 10.76 | 9.62 | 3.97 | 2.06 | — | — | 26.41 |
| Phenolic Monomers | 4.71 | 1.65 | 3.97 | 2.06 | — | — | 12.39 |
| Phenolic Oligomers | 6.05 | 7.97 | — | — | — | — | 14.02 |
| Light Organic Acids | — | — | — | — | 2.57 | 0.33 | 2.90 |

Example 4

Figure 6:
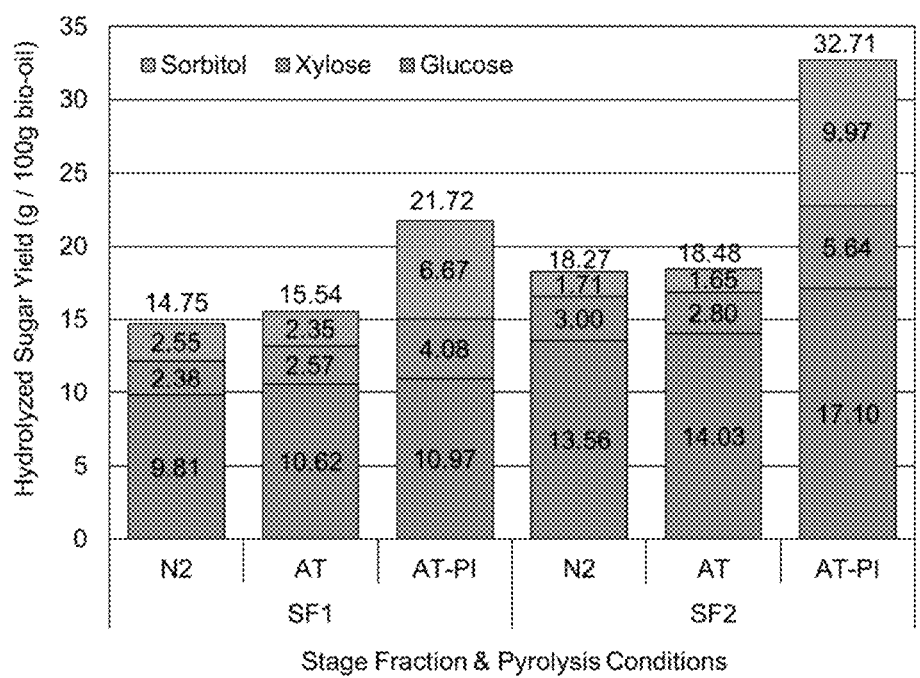
FIG. 6 shows the comparison of pyrolytic sugar content in bio-oil heavy ends produced during different pyrolysis conditions.
Figure 7:
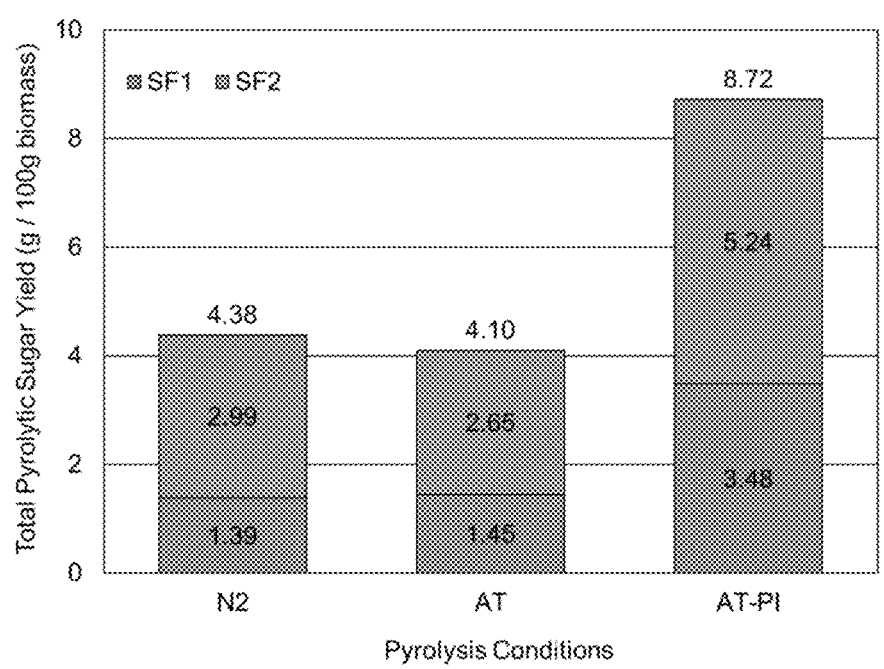
FIG. 7 shows a comparison of total pyrolytic sugar yields from red oak biomass during different pyrolysis conditions.

Increased Sugar Yields from Red Oak Biomass Pyrolysis Under AT-PI Conditions Compared to Baseline $N_2$ Pyrolysis and AT Pyrolysis The difference in $N_2$, AT, and AT-PI conditions significantly affected the system's production of bio-oil heavy ends including its quality and composition. In order to analyze the bio-oil's total pyrolytic sugar content, SF1 and SF2 bio-oil samples underwent acid-catalyzed hydrolysis in mini reaction vessels to convert pyrolytic sugars into the hydrolysis products, glucose, and xylose. Glucose, xylose, and sorbitol were analyzed and quantified by High-Performance Liquid Chromatography (HPLC) to compare the pyrolytic sugar content of bio-oil heavy ends from different conditions as seen in FIG. 6. $N_2$ and AT conditions produced bio-oils with similar pyrolytic sugar content but AT-PI produced bio-oil with significantly more sorbitol and xylose in SF1 and SF2. The increased sugar content coupled with higher mass yields of SF1 and SF2 bio-oil contributed to a two-fold increase in overall pyrolytic sugar yields from red oak biomass as seen in FIG. 7.

Example 5

Figure 8:
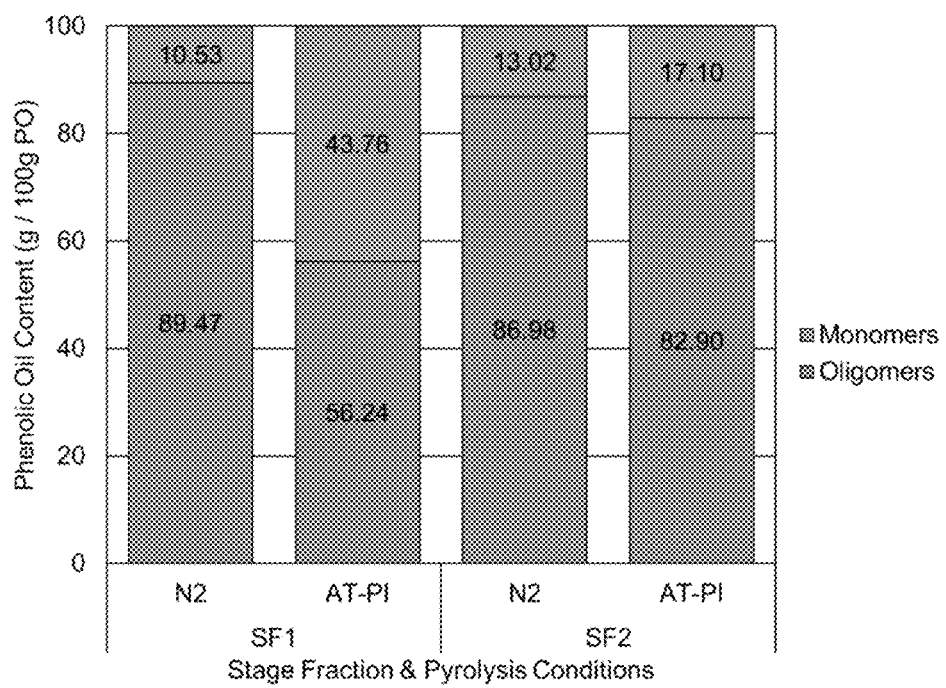
FIG. 8 shows a comparison of toluene-soluble phenolic monomers and toluene-insoluble phenolic oligomers in bio-oil heavy ends.

Increased Production of Bio-Oil Heavy Ends Under AT-PI Conditions Compared to Baseline $N_2$ Pyrolysis In order to investigate the phenolic products in bio-oil heavy ends, SF1 and SF2 bio-oil samples were washed with de-ionized water (1:1 mass ratio) to extract the majority of water-soluble sugars (Rover et al., "Production of Clean Pyrolytic Sugars for Fermentation," *ChemSusChem* 7:1662-1668 (2014), which is hereby incorporated by reference in its entirety). This mixture of water-soluble sugars and water-insoluble phenolic oil (PO) was decanted to produce a concentrated PO sample. These SF1 and SF2 PO samples underwent a second washing step using toluene (1:1 mass ratio) to extract phenolic monomers from the toluene-insoluble phenolic oligomers. This mixture was also decanted to compare the phenolic oil content of bio-oil heavy ends produced from different conditions as seen in FIG. 8. It appears that AT-PI conditions produced significantly more phenolic monomers in SF1 and slightly more in SF2 compared to baseline $N_2$ pyrolysis. This indicates that AT-PI either enhances lignin decomposition reactions, reduces phenolic oligomerization reactions, or some combination thereof. The observed increases in phenolic monomers agrees with prior oxidative pyrolysis research by Kim et al., "The Effect of Low-Concentration Oxygen in Sweep Gas During Pyrolysis of Red Oak Using a Fluidized Bed Reactor," *Fuel* 124:49-56 (2014) and Li et al., "Autothermal Fast Pyrolysis of Birch Bark with Partial Oxidation in a Fluidized Bed Reactor," *Fuel* 121:27-38 (2014), which are hereby incorporated by reference in their entirety.

Example 6

Comparison of Non-Condensable Gases from Various Pyrolysis Conditions

After condensable organic compounds have been collected as liquid products, NCG's are continually analyzed by gas chromatography (Agilent Varian CP-4900 Micro-GC model) to measure the concentrations of Nitrogen ($N_2$), Oxygen ($O_2$), Hydrogen ($H_2$), Helium (He), Carbon Monoxide (CO), Carbon Dioxide ($CO_2$), Methane ($CH_4$), Ethane ($C_2H_6$), and Ethylene ($C_2H_4$). The NCG's flow rate was determined by using a known mass flow rate of inert He as a tracer in the fluidizing gas. The yield of NCGs from biomass was calculated and the relative percent change in gas species was compared to baseline $N_2$ pyrolysis using Equation 1.

$$\text{Relative Percent Change} = \frac{Yield_{GasSpecies} - Yield_{N_2 Baseline}}{Yield_{N_2 Baseline}} \quad \text{(Equation 1)}$$

Figure 9:
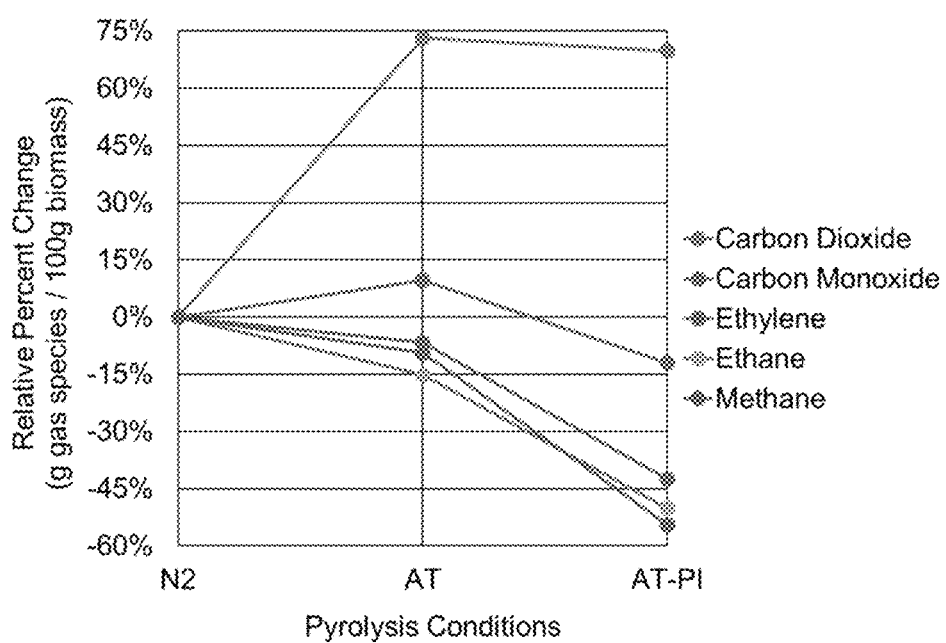
FIG. 9 shows a comparison of non-condensable gas products from different pyrolysis conditions.

A comparison of the relative percent changes for all carbonaceous gas compounds in NCGs is shown in FIG. 9. Carbon dioxide increased significantly for both AT and AT-PI conditions and indicates the presence of combustion reactions during the process. Methane, ethane, and ethylene all showed net decreases for both AT and AT-PI conditions and were consumed via combustion during the process. Carbon monoxide, which represents an incomplete combustion product, increased during AT pyrolysis but decreased for AT-PI conditions. For AT pyrolysis, it is believed that decomposition reactions (oxidative/thermal cracking) of heavy molecular weight bio-oil species could have resulted in net increases of CO while producing lower yields of bio-oil heavy ends previously seen in FIGS. 4 and 5. For AT-PI conditions, CO exhibits an overall net decrease in yield which indicates that it is consumed via combustion.

Discussion of Examples 1-6

Autothermal process intensification of biomass fast pyrolysis provides several benefits compared to traditional $N_2$ pyrolysis. This mode of operation overcomes the traditional heat transfer limitations encountered in fluidized reactor systems and allows for much higher biomass throughput. Direct, partial oxidation of the feedstock represents a simpler mode of heat transfer that can be scaled from pilot to demonstration and commercial systems. This also reduces and possibly eliminates the need for a secondary combustor that would otherwise be needed for process heat. Operating completely with air fluidization helps simplify the design of modular systems and represents an economic advantage over costly inert $N_2$.

Examples 1-6 provide results based on red oak pyrolysis experiments; pyrolysis of other biomass feedstocks may quantitatively, but not qualitatively, affect the system's throughputs since the operating equivalence ratio is largely dependent on the biomass' specific enthalpy of pyrolysis.

Heat transfer is the bottleneck to fast pyrolysis of biomass. Although the enthalpy for pyrolysis is relatively small (comparable to the enthalpy of evaporation for methanol), operation at temperatures around 500° C. constrains heat carriers to inert gases and granular media like sand or steel shot that can sustain only modest thermal fluxes in practical pyrolysis systems. With heat transfer controlling the rate of pyrolysis, reactor capacity only scales as the square of reactor diameter and does not benefit from economies of scale in building larger reactors. Applicants have eliminated this heat transfer bottleneck by replacing it with partial oxidation of biomass or pyrolysis products to provide the enthalpy of pyrolysis in a fluidized bed reactor, a process that can be described as autothermal pyrolysis. The amount of oxygen depends upon the biomass being pyrolyzed and parasitic heat losses in the reactor, but under conditions that simulate adiabatic operation, equivalence ratios are around 0.06, compared to 0.20 or higher for autothermal gasifiers. At these low equivalence ratios, there was no significant loss in bio-oil yield or quality when operating at similar throughput for the reactor operated in conventional, heat transfer limited mode. Removal of the heat transfer bottleneck allows processing of much more biomass through the pyrolyzer, reaching five times the capacity of the conventionally operated pyrolyzer, at which point the pyrolyzer can be "air blown" (100% air as the fluidization/ventilation gas). This very high throughput actually increased the yield of bio-oil, especially of anhydrosugars and phenolic oil. The examples of the present application indicate that oxidation of non-condensable gas species (CO, $CH_4$, $C_2H_6$, and $C_2H_4$) released during pyrolysis provides about half the energy for pyrolysis while the remainder of the energy is thought to come from partial oxidation of lignin.

Autothermal pyrolysis represents significant advance in process intensification for fast pyrolysis, allowing a several fold increase in the amount of biomass that can be processed in a reactor of given size. Autothermal operation also simplifies the design of pyrolysis reactors, eliminating heat exchangers, combustors, and nitrogen supply systems, reducing both capital and operating costs. Process intensification of pyrolysis makes possible the construction of smaller, modular systems suitable for distributed processing of dispersed biomass feedstocks.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A pyrolysis method comprising:
providing a biomass and
subjecting said biomass, in a reactor operating at a heat loss of less than 1% of the biomass' chemical energy content, to partial oxidation where, during steady state operation of the reactor, oxygen is provided to the reactor in sufficient quantity to achieve an equivalence ratio of 0.06 to 0.15 to release sufficient energy to support endothermic pyrolysis reactions and produce pyrolysis products comprising condensable organic compounds, wherein the condensable organic compounds are the major portion of the pyrolysis products and the major portion comprises at least about 50% of the total pyrolysis products.

2. The method of claim 1, wherein said subjecting is effective to increase the level of biomass throughput in the reactor, during steady state operation, by a value proportional to more than the reactor's diameter squared, as compared to when said subjecting is carried out in the absence of partial oxidation.

3. The method of claim 2, wherein said subjecting is effective to increase the level of biomass throughput in the reactor, during steady state operation, by a value proportional to up to and optionally including, the reactor's diameter cubed, as compared to when said subjecting is carried out in the absence of partial oxidation.

4. The method of claim 1, wherein the condensable organic compounds have a residence time in the reactor of 2-5 seconds.

5. The method of claim 1, wherein said subjecting is carried out in a well-mixed reactor.

6. The method of claim 5, wherein the well-mixed reactor is a fluidized bed reactor.

7. The method of claim 1, wherein the production of condensable organic compounds is achieved with little or no loss in bio-oil yield or quantity compared to when oxygen is not provided to the reactor.

8. The method of claim 1, wherein the major portion of the pyrolysis products comprises bio-oil.

9. The method of claim 1, wherein the reactor is insulated and constructed to reduce the reactor's intrinsic surface area to volume ratio.

10. The method of claim 1, wherein the biomass is selected from the group consisting of forest and mill residues, agricultural crops and wastes, wood and wood wastes, grasses, manure, livestock operation residues, trees and plants, and municipal and industrial wastes.

11. The method of claim 1, wherein said subjecting is carried out at a temperature of 400 to 600° C.

12. The method of claim 1, wherein the partial oxidation is carried out with air or air/nitrogen mixtures.

13. The method of claim 1 further comprising:
recovering said condensable organic compounds after said subjecting.

14. The method of claim 13, wherein the recovered condensable organic compounds contain 5 to 15 wt % pyrolytic sugars.

15. The method of claim 13, wherein the recovered condensable organic compounds contain 45 to 60 wt % phenolics.

16. The method of claim 1 further comprising:
recovering biochar produced in the reactor after said subjecting.

17. The method of claim 1, wherein the reactor is provided with a heater to enable the reactor to reach steady state operation and enable the reactor to operate adiabatically during such steady state operation.

18. The method of claim 1, wherein said subjecting produces condensable organic compounds and said method further comprises:
cooling the condensable organic compounds in a first stage comprising a condenser having passages for the condensable organic compounds separated by a heat conducting wall from passages for a coolant, wherein the coolant in the condenser of the first stage is maintained at a substantially constant temperature, set at a temperature in the range of 75 to 130° C., to condense a first liquid fraction of liquefied bio-oil constituents in the condenser of the first stage and
collecting the first liquid fraction of liquefied bio-oil constituents from the condenser of the first stage.

19. The method of claim 18 further comprising:
recovering a first bio-oil vapor fraction from the condenser of the first stage and
removing aerosols from the first bio-oil vapor fraction in a second stage as a second liquid fraction of liquefied bio-oil constituents.

20. The method of claim 19 further comprising:
recovering a second bio-oil vapor fraction after said removing aerosols;
cooling the second bio-oil vapor fraction in a third stage comprising a condenser having passages for the second bio-oil vapor fraction separated by a heat conducting wall from passages for a coolant, wherein the coolant in the condenser of the third stage is maintained at a substantially constant temperature, set at a temperature above the dew point of water, to condense a third liquid fraction of liquefied bio-oil constituents in the condenser of the third stage; and
collecting the third liquid fraction of liquefied bio-oil constituents from the condenser of the third stage.

21. The method of claim 20 further comprising:
recovering a third bio-oil vapor fraction from the third stage and
removing aerosols from the third bio-oil vapor fraction in a fourth stage as a fourth liquid fraction of liquefied bio-oil constituents.

22. The method of claim 21 further comprising:
recovering a fourth bio-oil vapor fraction after said removing aerosols from the third bio-oil vapor fraction;
cooling the fourth bio-oil vapor fraction in a condenser of a fifth stage having passages for the fourth bio-oil vapor separated by a heat conducting wall from passages for a coolant, wherein the coolant in the condenser of the fifth stage is maintained at a substantially constant temperature, with a temperature set sufficiently low to condense substantially all water vapor from the fourth bio-oil vapor as a fifth liquid fraction of liquefied bio-oil constituents in the condenser of the fifth stage; and
collecting the fifth liquid fraction of liquefied bio-oil constituents from the condenser of the fifth stage.

23. The method of claim 1, wherein said subjecting produces condensable organic compounds and said method further comprises:
cooling the condensable organic compounds in a liquid scrubbing system to condense a first liquid fraction of liquefied bio-oil constituents and
collecting the first liquid fraction of liquefied bio-oil constituents from the liquid scrubbing system.

* * * * *